United States Patent
Caruso (12)

(10) Patent No.: US 6,277,398 B1
(45) Date of Patent: Aug. 21, 2001

(54) ANALGESIC DRUG COMPOSITION CONTAINING A CAPSAICINOID AND POTENTIATOR THEREFOR

(75) Inventor: Frank S. Caruso, Colts Neck, NJ (US)

(73) Assignee: Endo Pharmaceuticals Inc., Chadds Ford, PA (US)

(*) Notice: Subject to any disclaimer, the term of this patent is extended or adjusted under 35 U.S.C. 154(b) by 0 days.

(21) Appl. No.: 09/441,268

(22) Filed: Nov. 16, 1999

Related U.S. Application Data

(63) Continuation of application No. PCT/US98/10769, filed on May 26, 1998
(60) Provisional application No. 60/048,314, filed on May 27, 1997.

(51) Int. Cl.[7] .......................... A61F 13/00; A61F 13/02; A61L 15/16
(52) U.S. Cl. .......................... 424/443; 424/449; 424/448
(58) Field of Search .................... 424/443, 449; 514/165, 582

(56) References Cited

U.S. PATENT DOCUMENTS

| | | |
|---|---|---|
| 4,446,140 * | 5/1984 | Nelson ........................ 424/260 |
| 4,455,146 | 6/1984 | Noda et al. . |
| 4,557,934 | 12/1985 | Cooper . |
| 4,599,342 * | 7/1986 | LaHann ........................ 514/282 |
| 4,812,446 * | 3/1989 | Brand ........................ 514/165 |
| 5,273,757 | 12/1993 | Jaeger et al. . |
| 5,332,576 | 7/1994 | Mantelle . |
| 5,336,213 | 8/1994 | D'Angelo et al. . |
| 5,505,958 | 4/1996 | Bello et al. . |
| 5,589,180 | 12/1996 | Hind . |
| 5,716,621 * | 2/1998 | Bello et al. ........................ 424/443 |

FOREIGN PATENT DOCUMENTS

| | | |
|---|---|---|
| 97/02273 | 1/1997 | (WO) . |
| 97/04780 | 2/1997 | (WO) . |
| WO 97/04780 * | 2/1997 | (WO) ........................ A61K/31/485 |
| 97/10815 | 3/1997 | (WO) . |
| 98/00117 | 1/1998 | (WO) . |

* cited by examiner

*Primary Examiner*—Thurman K. Page
*Assistant Examiner*—Isis Ghali
(74) *Attorney, Agent, or Firm*—Dilworth & Barrese, LLP

(57) ABSTRACT

The analgesic effectiveness of a capsaicinoid such as capsaicin is potentiated by an analgesic potentiator selected from the group consisting of dextromethorphan, dextrorphan and pharmaceutically acceptable salts thereof.

16 Claims, 1 Drawing Sheet

ANALGESIC DRUG COMPOSITION CONTAINING A CAPSAICINOID AND POTENTIATOR THEREFOR

This is a continuation of copending application Ser. No. PCT/US98/10769 filed May 26, 1998 and also claims the benefit of Provisional No. 60/048,314 filed May 27, 1997.

BACKGROUND OF THE INVENTION

This invention relates to analgesic drugs and methods of inducing analgesia. More particularly, this invention relates to an analgesic drug containing, as an analgesic component, at least one capsaicinoid and, as a potentiator for the capsaicinoid, dextromethorphan, dextrorphan and/or pharmaceutically acceptable salt thereof.

Capsicum oleoresin, an extract of capsicum (dried red pepper and other species of the genus Capsicum such as *Capsicum frutescens* and *Capsicum annum*), contains the capsaicinoid capsaicin (trans-8-methyl-N-vanillyl-6-noneamide). Both capsicum oleoresin and capsicum have for many years been used in a variety of over-the-counter topical analgesic medications such as HEET, INFRA-RUB, OMEGAOIL, and SLOAN's LINIMENT. See also, U.S. Pat. No. 3,880,996 which discloses a topically administered analgesic compositions for the symptomatic relief of localized pain of musculo-skeletal etiology containing, inter alia, capsicum oleoresin.

Cutaneous pain and other sensations of inflammatory pain are thought to be mediated by substance P, an endogenous neuropeptide. Capsaicin enhances the release of substance P from neurons preventing its reaccumulation. As a result of this effect, capsaicin is believed to render skin insensitive to pain by depleting substance P from peripheral sensory neurons. See, Jessell et al., "Capsaicin-induced depletion of substance P from primary sensory neurones", *Brain Research*, 152 (1978) 183–188.

Combinations of capsaicin and an opioid analgesic such as morphine, codeine, hydromorphone, oxycodone, hydrocodone, oxymorphone, propoxyphene, levorphanol, meperidine, fentanyl, methadone, pentazocine, butorphanol and nalbuphine are disclosed in U.S. Pat. No. 4,599,342, combinations of capsaicin and a nonsteroidal antiinflammatory, antipyretic and analgesic drug such as aspirin, salicylic acid, sodium salicylate, methyl salicylate, diflusinal, phenylbutazone, indomethacin, zomapirac acid, sulindac, fluproquazone, mefenamic acid, ibuprofen, naproxen, ketoprofen, fenoprofen, suprofen, flurbiprofen benoxaprofen, pirprofen, carpoprofen, acetaminophen and phenacetin are disclosed in U.S. Pat. No. 4,681,897 and combinations of capsaicin with the local anesthetic lidocaine or benzocaine are disclosed in U.S. Pat. No. 4,997,843.

Delivery vehicles for topically administered drugs such as capsaicin and capsicum include the gels disclosed in U.S. Pat. Nos. 5,178,879, 5,306,504 and 5,420,197. A non-occlusive adhesive patch for the topical administration of capsicum or other topical medication is disclosed in U.S. Pat. No. 5,536,263 and in commonly assigned copending U.S. patent application Ser. No. 08/675,348, filed Jul. 3, 1996.

Dextromethorphan is a common ingredient of cough, cold and flu medications due to its antitussive (cough-suppressing) activity. Dextromethorphan is widely and authoritatively regarded as lacking analgesic activity, one of several pharmacological properties that distinguishes it from the opiate analgesics of the morphine type to which it is structurally related. Thus, Goodman and Gilman's "The Pharmaceutical Sciences", 17th ed., Mack Pub. (1985), page 870 states that "unlike codeine, [dextromethorphan] is devoid of analgesic properties . . . ", "Drug Evaluation Annual 1998", American Medical Association, 1994, page 469 states that dextromethorphan ". . . does not have additive, analgesic, or sedative actions . . . " and Kirk-Othmer, "Encylopedia of Chemical Technology", 3rd ed., Vol. 9, John Wiley & Sons (1980), page 551, states that "[i]n the case of 3-methoxy-N-methylmorphinan, the levorotatory isomer was found to possess both analgetic and antitussive activity whereas the dextrorotatory isomer (dextromethorphan (37)) possessed only antitussive activity." Unlike the opioid analgesics, dextromethorphan in therapeutic dosages does not produce respiratory depression. Even the antitussive effects of dextromethorphan differ from those of the opioid analgesics; thus, e.g., the antitussive effects of the opioid analgesic codeine are antagonized by naloxone but those of dextromethorphan are not. And, unlike the opioid analgesics, dextromethorphan poses so little risk of abuse that it is specifically stated to be a non-scheduled drug (21 U.S.C. §811(g)(2)).

The few known exceptions to dextromethorphan's lack of analgesic activity involve specific pain conditions, e.g., mouth pain as disclosed in U.S. Pat. No. 4,446,140, dysmenorrhea (vaginal cramps) as disclosed in EPA 81,823 and chronic pain as disclosed in U.S. Pat. No. 5,352,683. More recently it has been disclosed in PCT publication WP 96/07412 that while dextromethorphan does not have general analgesic usefulness when administered alone, it significantly enhances, or potentiates, the analgesic activity of a nonsteroidal antiinflammatory drug (NSAID) or acetaminophen with which it is administered for all types of pain.

SUMMARY OF THE INVENTION

It is an object of the invention to provide an analgesic drug composition containing, as an analgesic component, a capsaicinoid such as capsaicin and, as a potentiator for the capsaicinoid, dextromethorphan, its active metabolite dextrorphan and/or pharmaceutically acceptable salt thereof.

It is a particular object of the invention to provide various dosage forms of the foregoing analgesic drug composition including those suitable for oral, parenteral, topical, etc., administration.

It is yet a further object of the invention to provide a nonocclusive drug delivery device for topical administration of the analgesic drug composition herein.

In keeping with these and other objects of the invention, there is provided an analgesic drug composition comprising an analgesia-inducing amount of at least one capsaicinoid possessing analgesic activity and an analgesia-potentiating amount of at least one analgesic potentiator selected from the group consisting of dextromethorphan, dextrorphan and pharamaceutically acceptable salts thereof.

The expression "analgesia-inducing amount" as applied to the capsaicinoid component of the foregoing drug composition shall be understood to mean an amount of capsaicinoid which when administered by itself or in combination with the analgesic potentiator provides significant analgesic effect.

DESCRIPTION OF THE PREFERRED EMBODIMENTS

Figure 1:
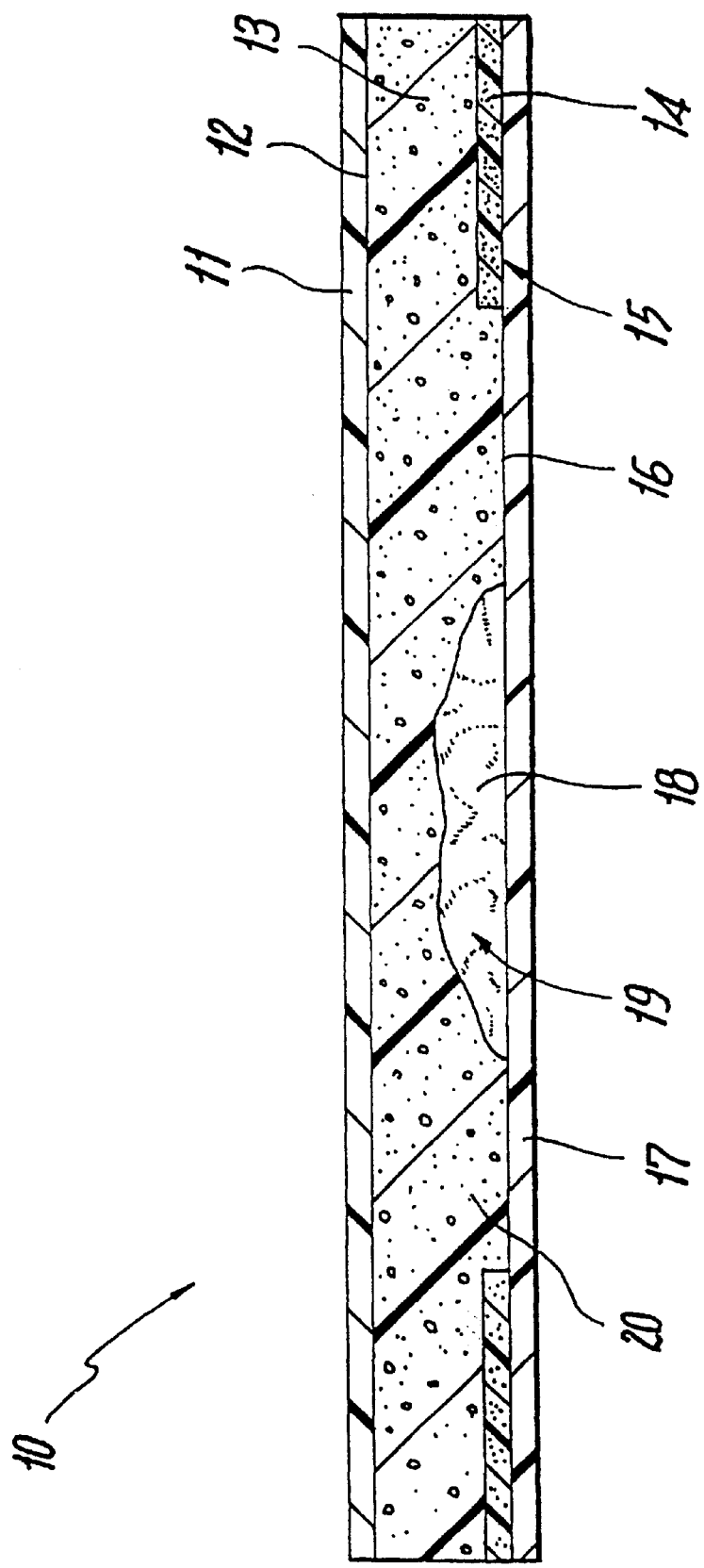
FIG. 1 is a cross-sectional view of a nonocclusive drug delivery system which can be used for the topical administration of the analgesic drug composition of this invention.

Among the analgesic capsaicinoids that can be used herein are those of the general formula

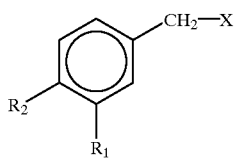

wherein $R_1$ is selected from the group consisting of OH and $OCH_3$, $R_2$ is selected from the group consisting of OH and

$R_3$ is selected from the group consisting of a $C_1$–$C_4$ alkyl, phenyl and methyl, X is selected from the group consisting of

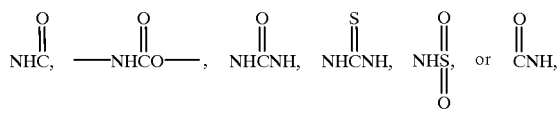

and R is selected from the group consisting of a $C_5$–$C_{11}$ alkyl, $C_5$–$C_{11}$ alkenyl, $C_{11}$–$C_{23}$ cis alkenyl, $C_{11}$–$C_{23}$ alkynyl, C–$C_{23}$ alkadienyl and $C_{11}$–$C_{23}$ methylene substituted alkane.

Preferred capsaicinoids of the foregoing structure include those wherein both $R_1$ and $R_2$ are OH and X is

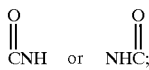

and those wherein $R_1$ is $OCH_3$, $R_2$ is OH or

Preferred R groups include $C_7$–$C_{10}$ alkyls and trans alkenyls, and $C_{16}$–$C_{21}$ cis alkenyls and alkadienyls. The preferred moieties within these groups include $C_8H_{17}$, $C_9H_{17}$ and $C_{17}H_{33}$. Preferred capsaicinoids include N-vanillyl-alkadienamides, N-vanillyl-alkanedienyls, and N-vanillyl-cis-monounsaturated alkenamides. Among the capsaicinoids that are preferred for use herein are capsaicin (trans-8-methyl-N-vanillyl-6-noneamide) or capsaicin-containing substance such as capsicum oleoresin and capsicum, synthetic capsaicin (N-vanillylnonanamide), the N-[(substituted phenyl)methyl] alkynylamides of U.S. Pat. No. 4,532,139, the methylene substituted-N-[(substituted phenyl)methyl]-alkanamides of U.S. Pat. No. 4,544,668, the N-[(substituted phenyl)methyl]diunsaturated amides of U.S. Pat. No. 4,544,669, the nonanoyl vanillylamide succinate of U.S. Pat. No. 5,094,782, the N-[(substituted phenyl)methyl]-cis-monounsaturated alkenamides of U.S. Pat. No. 5,593,848, the N-vanillylureas of EPA 68,590, the N-vanillylsulfonamides of EPA 68,591, the N-vanillylcarbamates of EPA 68,592 and the hydroxyphenylacetamides of EPA 89,710.

Of the foregoing capsaicinoids, capsaicin is the most preferred.

As stated above, the selected capsaicinoid component of the analgesic drug composition of this invention is potentiated by dextromethorphan, dextrorphan or pharmaceutically acceptable thereof, e.g., such acid addition salts as dextromethorphan hydrobromide and dextrorphan hydrobromide. Of the foregoing, dextromethorphan hydrobromide is preferred due to its ready commercial availability and long history of use in numerous over-the-counter medications.

The analgesic drug composition of this invention must contain an analgesia-inducing amount of capsaicinoid(s), considered to be that amount of capsaicinoid(s) which, if administered alone, will provide significant analgesic effect or, if below that amount, when administered with the analgesic potentiator will provide significant analgesic effect. Thus, the analgesic potentiator component of the drug composition herein permits the capsaicinoid to be present in an amount which would be ineffective or at best only marginally effective to induce analgesia were it to be administered alone or, if the capsaicinoid is already at a level which by itself would provide significant analgesic effect, the presence of the potentiator will result in a significant increase in the level and/or duration of analgesia.

With capsaicin as illustrative, the drug composition herein when intended for administration to adult humans can contain from about 0.02 to about 1.0, and preferably from about 0.025 to about 0.05, weight percent capsaicinoid(s).

The amount of analgesia potentiator present in the analgesic drug composition of this invention must be at least that which is effective to significantly increase the analgesic effectiveness of the capsaicinoid. With dextromethorphan hydrobromide as illustrative, doses of the analgesic potentiator can vary from about 0.2 to about 2, and preferably from about 0.5 to about 1.0, weight percent.

In addition to the capsaicinoid(s) and analgesic potentiator, the analgesic drug composition of this invention can contain one or more additional drug components, e.g., an analgesic of the opioid type as disclosed in U.S. Pat. No. 4,599,342, an analgesic of the nonopioid type as disclosed in U.S. Pat. No. 4,997,843, a counterirritant (other than a capsaicinoid or source thereof) such as camphor or menthol, a local vasodilator such as histamine dihydrochloride and methyl nicotinate, etc., present in the usual amounts.

The analgesic drug composition can be formulated for oral, parenteral, topical, etc., administration. Depending upon the particular route of administration, a variety of pharmaceutically-acceptable carriers, well known in the art, can be used to prepare the formulations. These include solid or liquid fillers, diluents, hydrotropes, surface-active agents, and the like. The amount of carrier employed in conjunction with the capsaicinoid and analgesic potentiator will be such as to provide a practical quantity of these drugs per unit dose.

The drug composition of this invention is especially useful for the treatment of such pains as neuralgias, rheumatoid arthritis, bursitis, myositis, integumental pain, etc., for which it is administered as a topical preparation, preferably in combination with a penetration enhancer. The drug composition can be formulated as a liquid, paste, ointment, cream, lotion, or gel, e.g., any of the gels disclosed in U.S. Pat. Nos. 5,178,879, 5,306,504 and 5,420,197.

The following oleophilic topical ointment provides generally acceptable results:

| Component | Amount (g) |
| --- | --- |
| capsaicin | 0.025–0.25 |
| dextromethorphan hydrobromide | 0.5–1.0 |

-continued

| Component | Amount (g) |
| --- | --- |
| white wax | 5–20 |
| petrolatum | q.s. to 100 |

The analgesic drug composition can be administered via a non-occlusive adhesive patch, e.g., as disclosed in U.S. Pat. No. 5,536,263 and preferably as disclosed in commonly assigned copending U.S. patent application Ser. No. 08/675,348, filed Jul. 3, 1996.

An embodiment of the nonocclusive delivery device of Ser. No. 08/675,348 is shown generally in FIG. 1 at 10. The drug delivery device includes a substantially moisture vapor permeable, liquid impermeable, flexible thermoplastic barrier layer 11 bonded to, and generally coextensive with, upper surface 12 of open cell, flexible, oleophilic thermoplastic resin foam layer 13. Pressure sensitive adhesive 14 occupies a zone, or stratum, 15 on lower surface 16 of foam layer 13 for securing the drug delivery device to the skin. Drug composition 18, which is formulated within an oleophilic delivery vehicle, occupies drug depot zone 19 and is separated from adhesive zone 15 by barrier zone 20 which prevents or inhibits migration of the drug composition into adhesive 14. A release liner 17 seals and protects lower surface 16 of the foam layer during the residency of drug delivery device 10 within its package. The minimum strength of the bond between barrier layer 11 and foam layer 13 must be sufficient to prevent or inhibit separation, i.e., delamination, of the barrier layer from the foam layer under the sort of flexing and/or stretching forces that may be encountered during the useful life of the applied device. In general, bond strengths of at least about 2 newtons (N), preferably at least about 3 N and more preferably at least about 5 N will generally provide satisfactory results in this regard. However the bond between layers 11 and 13 may be achieved, it is necessary that the bond itself not result in a significant reduction in the moisture vapor transmission rate (MVTR) of the assembled layers. While known and conventional contact adhesives can readily provide barrier layer-to-foam layer bond strengths of 2 N and greater, they may be disadvantageous in reducing the MVTR of the assembled layers to an unacceptable degree. Accordingly, it is preferred to employ a nonadhesive bonding technique, e.g., one employing heat such as flame bonding that is capable of producing the desired bond strengths but without significantly reducing the MVTR of the composite formed from layers 11 and 13. In general, the MVTR of the barrier layer-foam layer subassembly will be at least about 500, preferably at least about 1000 and more preferably at least about 1200, $g/m^2/24$ h at 100% r.h. and 32° C. as measured by ASTM F1249-90.

Another requirement of drug delivery device 10 is that whatever the bond strength between barrier layer 11 and foam layer 13, the contact adhesive must impart a peel strength to the drug delivery device, i.e., the amount of force required to peel the spent drug delivery device from the skin, which is less, preferably at least about 20 percent less and more preferably at least about 40 percent less, than such bond strength in order to prevent or minimize the separation of the barrier layer from the foam layer when the spent drug delivery device is peeled from the skin. Barrier layer 11 can be any thermoplastic film possessing an MVTR of one of the aforestated values. Preferably, the barrier layer can be a polyurethane film possessing an average thickness of from about 0.5 to about 3.5 mils and preferably from about 1.0 to about 1.5 mils and a tensile strength of at least about 2500 psi and preferably at least about 3500 psi.

Foam layer 13 in its as-manufactured state is an open cell, flexible, oleophilic foam that provides a stable matrix for the analgesic drug composition herein particularly when the drug is formulated in an oleophilic delivery vehicle. By "stable matrix" is meant that property of the foam which, owing to its oleophilic character, enables the foam to function not only as a depot, or reservoir, for the oleophilic drug composition, but confines the composition to zone 19 which is separated by barrier zone 20 from zone 15 occupied by pressure sensitive adhesive 14. Thus, the oleophilic characteristics of the foam layer prevent or inhibit migration of drug composition 18 into adhesive zone 15 where it could destroy or impair the effectiveness of adhesive 14 in securing the drug delivery device to the skin. Another advantageous characteristic of the drug delivery device herein is its ability to maintain continuous contact between the drug composition and the skin thus assuring that the drug will be constantly available at the site of its administration.

In general, the useful foams possess a density of from about 0.8 to about 8.0 and preferably from about 1.2 to about 4.8 lb/ft, a number of pores per inch of from about 30 to about 120 and preferably from about 60 to about 90, and can be fully or partially reticulated or nonreticulated. The average thickness of the foam layer can vary from about 30 to about 100 mils and for many applications is preferably from about 40 to about 70 mils. Suitable foams that can be employedherein include the untreated oleophilic (i.e., hydrophobic) open cell polyurethane foams disclosed in U.S. Pat. No. 5,352,711.

Pressure sensitive adhesive 14 can be selected from any of the known and conventional medical grade adhesives, e.g., those based on polyacrylic, polyvinylether, or polyurethane resins. It is an essential requirement that the amount of adhesive 14 applied to zone 15 of foam layer 13 be sufficient to achieve an acceptable level of adhesion of drug delivery device 10 to the skin but, as previously stated, with a resulting peel strength that is sufficiently below the bond strength between the barrier and foam layers. The amount of adhesive that will satisfy these criteria can be readily determined by simple and routine testing. Ordinarily, a medical grade polyacrylic adhesive such as Durotak® (National Starch & Chemical Company, Bridgewater, N.J.) or Gelva® (Monsanto Inc., St. Louis, Mo.) applied to a thickness of from about 1 to about 3.5 mils and preferably from about 2.0 to about 2.5 mils (depending, of course, on the thickness of the foam layer), or applied at a rate of from about 25 to about 100 $g/cm^2$ and preferably from about 50 to about 65 $g/cm^2$, will meet these requirements reasonably well.

What is claimed is:

1. An analgesic drug composition comprising an analgesia-inducing amount of at least one capsaicinoid possessing analgesic activity and an analgesia-potentiating amount of at least one analgesic potentiator selected from the group consisting of dextromethorphan, dextrorphan and pharmaceutically acceptable salts thereof.

2. The analgesic drug composition of claim 1 wherein the capsaicinoid possesses the general formula

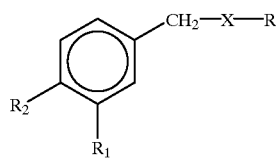

wherein $R_1$ is selected from the group consisting of OH and $OCH_3$, $R_2$ is selected from the group consisting of OH and

$R_3$ is selected from the group consisting of a $C_1$–$C_4$ alkyl, phenyl and methyl, X is selected from the group consisting of

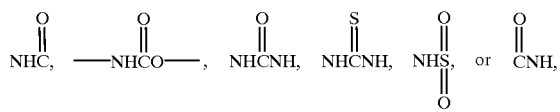

and R is selected from the group consisting of a $C_5$–$C_{11}$ alkyl, $C_5$–$C_{11}$ alkenyl, $C_{11}$–$C_{23}$ cis alkenyl, $C_{11}$–$C_{23}$ alkynyl, C–$C_{23}$ alkadienyl and $C_{11}$–$C_{23}$ methylene substituted alkane.

3. The analgesic drug composition of claim 1 wherein the capsaicinoid is capsaicin.

4. The analgesic drug composition of claim 1 in a topical drug delivery dosage form.

5. The analgesic drug composition of claim 4 containing a penetration chamber.

6. The analgesic drug composition of claim 4 in an oleophilic carrier.

7. The analgesic drug composition of claim 4 wherein the capsaicinoid is capsaicin.

8. The analgesic drug composition of claim 4 wherein the analgesic potentiator is dextromethorphan or pharmaceutically acceptable salt thereof.

9. A nonocclusive drug delivery device for the delivery of a capsaicinoid-containing analgesic drug composition which comprises:
   a) an open cell, flexible, oleophilic thermoplastic resin foam layer possessing upper and lower surfaces and predetermined adhesive and drug depot zones, the drug depot zone containing an analgesia-inducing amount of a capsaicinoid-containing analgesic drug composition which comprises at least one capsaicinoid possessing analgesic activity and an analgesia-potentiating amount of at least one analgesia potentiator selected from the group consisting of dextromethorphan, dextrorphan and pharmaceutically acceptable salts thereof;
   b) a substantially moisture vapor permeable, liquid impermeable, flexible thermoplastic barrier layer bonded to the upper surface of the foam layer, the composite of the barrier and foam layers possessing a moisture vapor transmission rate of at least about 500 $g/m^2/24$ h at 100% r.h and 32° C., the bond strength between the barrier layer and the foam layer being such as to resist separation of the barrier layer from the foam layer when the drug delivery device is subjected to the flexing and/or stretching forces normally encountered during its useful applied life; and,
   c) a pressure sensitive adhesive within the adhesive zone of the foam layer, the adhesive layer imparting a peel strength to the drug delivery device which is sufficiently below that of the bond strength between the foam layer and the barrier layer such that upon peeling the device from the skin, substantially all of the foam layer remains bonded to the barrier layer.

10. The drug delivery device of claim 9 wherein the capsaicinoid is capsaicin.

11. The drug delivery device of claim 10 in an oleophilic carrier.

12. The drug delivery device of claim 10 wherein the analgesic potentiator is dextromethorphan or pharmaceutically acceptable salt thereof.

13. A method for inducing analgesia in a mammal which comprises topically administering to a mammal in need of analgesia an analgesic drug composition comprising an analgesia-inducing amount of at least one capsaicinoid possessing analgesic activity and an analgesia-potentiating amount of at least one analgesic potentiator selected from the group consisting of dextromethorphan, dextrorphan and pharmaceutically acceptable salts thereof.

14. The method of claim 13 wherein the capsaicinoid is capsaicin.

15. The method of claim 14 wherein the analgesic potentiator is dextromethorphan or pharmaceutically acceptable salt thereof.

16. The method of claim 13 wherein the analgesic drug composition is delivered by the nonocclusive drug delivery device which comprises:
   a) an open cell, flexible, oleophilic thermoplastic resin foam layer possessing upper and lower surfaces and predetermined adhesive and drug depot zones, the drug depot zone containing an analgesia-inducing amount of the analgesic drug composition:
   b) a substantially moisture vapor permeable, liquid impermeable, flexible thermoplastic barrier layer bonded to the upper surface of the foam layer, the composite of the barrier and foam layers possessing a moisture vapor transmission rate of at least about 500 $g/m^2/24$ h at 100% r.h and 32° C., the bond strength between the barrier layer and the foam layer being such as to resist separation of the barrier layer from the foam layer when the drug delivery device is subjected to the flexing and/or stretching forces normally encountered during its useful applied life; and,
   c) a pressure sensitive adhesive within the adhesive zone of the foam layer, the adhesive layer imparting a peel strength to the drug delivery device which is sufficiently below that of the bond strength between the foam layer and the barrier layer such that upon peeling the device form the skin, substantially all of the foam layer remains bonded to the barrier layer.

* * * * *